United States Patent
Sun et al.

(10) Patent No.: US 9,301,673 B2
(45) Date of Patent: Apr. 5, 2016

(54) VAGINAL DILATOR FOR USE IN GYNECOLOGIC EXAMINATION

(71) Applicant: GUANGZHOU YULIN PHARMACEUTICAL CO., LTD., Guangdong (CN)

(72) Inventors: Changchun Sun, Guangdong (CN); Minglei Zhang, Guangdong (CN); Lei Ge, Guangdong Province (CN)

(73) Assignee: Changchun Sun, Guangzhou (CN)

( * ) Notice: Subject to any disclaimer, the term of this patent is extended or adjusted under 35 U.S.C. 154(b) by 1 day.

(21) Appl. No.: 14/568,793

(22) Filed: Dec. 12, 2014

(65) Prior Publication Data
US 2015/0282696 A1   Oct. 8, 2015

(30) Foreign Application Priority Data

Apr. 4, 2014 (CN) .................... 2014 2 0166878 U

(51) Int. Cl.
*A61B 1/32* (2006.01)
*A61B 1/06* (2006.01)
*A61B 17/02* (2006.01)

(52) U.S. Cl.
CPC ............... *A61B 1/06* (2013.01); *A61B 17/0206* (2013.01); *A61B 17/0218* (2013.01)

(58) Field of Classification Search
CPC ............... A61B 17/02–17/0293; A61B 17/42; A61B 1/32; A61B 1/303
USPC .................................................. 600/201–235
See application file for complete search history.

(56) References Cited

U.S. PATENT DOCUMENTS

| | | | | |
|---|---|---|---|---|
| 449,941 A * | 4/1891 | Lee | ............... | 600/222 |
| 596,399 A * | 12/1897 | Fox | ............... | 600/205 |
| 1,066,889 A * | 7/1913 | Drosin | ............ | 600/222 |
| 3,789,835 A * | 2/1974 | Whitman | ........... | 600/223 |
| 4,597,383 A * | 7/1986 | VanDerBel | ...... | A61B 1/07 600/223 |
| 5,458,595 A * | 10/1995 | Tadir et al. | .......... | 606/15 |
| 6,432,049 B1 * | 8/2002 | Banta et al. | ........ | 600/249 |
| 2003/0176772 A1 * | 9/2003 | Yang | ................ | 600/220 |
| 2008/0228038 A1 * | 9/2008 | McMahon et al. | ......... | 600/223 |
| 2009/0076334 A1 * | 3/2009 | Chen | ......... | A61B 1/303 600/223 |
| 2009/0177044 A1 * | 7/2009 | Cohen | ......... | A61B 1/303 600/220 |
| 2009/0326331 A1 * | 12/2009 | Rosen | ......... | A61B 1/32 600/224 |

OTHER PUBLICATIONS

People's Republic of China Allowance Notification of Utility Model Patent issued in Chinese Patent Application No. 201420166878.8 dated Jul. 25, 2014, 2 pages.

* cited by examiner

*Primary Examiner* — Jan Christopher Merene
*Assistant Examiner* — Steven Cotroneo
(74) *Attorney, Agent, or Firm* — Staas & Halsey LLP

(57) ABSTRACT

A vaginal dilator for use in gynecologic examination. The vaginal dilator comprises an upper dilating member and a lower dilating member that are hinged to each other, the upper dilating member comprising an upper dilating leaf and an upper press rod arranged at a tail portion of the upper dilating leaf, the lower dilating member comprising a lower dilating leaf and a lower press rod arranged at a tail portion of the lower dilating leaf. The upper dilating leaf is hinged to the upper press rod, and the upper rod is hinged to the lower dilating member, and the upper press rod is provided with a light emitting element, a switch and a power source, the switch being connected with the light emitting element. The upper dilating leaf is pressed down to contact and mate with the upper press rod or the upper dilating leaf is disengaged from the upper press rod to coordinately control the switch to be connected to or disconnected from the power source.

14 Claims, 4 Drawing Sheets

VAGINAL DILATOR FOR USE IN GYNECOLOGIC EXAMINATION

CROSS-REFERENCE TO RELATED APPLICATIONS

This application claims priority benefit from Chinese utility model application No. 201420166878.8 filed on Apr. 4, 2014 in the State Intellectual Property Office of the People's Republic of China issued on Sep. 3, 2014 as ZL 201420166878.8, the disclosure of which is incorporated herein by reference in its entirety.

BACKGROUND OF THE INVENTION

1. Field of the Invention

One or more embodiments relate to an instrument for use in gynecologic examination, and in particular, to a vaginal dilator for use in gynecologic examination.

2. Description of the Related Art

A vaginal dilator is an instrument commonly used for routine gynecologic examination. A doctor also needs assistance by a light source during examining a patient's vagina. At present, a conventional vaginal dilator has been provided with a light source. Typically, some vaginal dilators have a fixed lamp, wherein the lamp is connected to a battery box via an electrical wire. However, in this design, the structure of the vaginal dilator is not compact and is not simple in operation. In addition, some vaginal dilators have a light source arranged on a leaf thereof. The light source is connected to the two poles of the power source, and an insulating gasket that can be removed is arranged between the poles and an LED light source. Opening of the LED lamp is achieved by removing the insulating gasket. However, upon the opening of the lamp, the lamp is steadily on until the battery is exhausted. Consequently, it is not convenient for a medical staff to control the light source and it is also unfavorable to saving of energy and reuse of the power source.

Accordingly, there is a need for a vaginal dilator which implements control of operation of the light source, is simple in operation, compact in structure, and provides sufficient light source to facilitate examination

SUMMARY OF THE INVENTION

Therefore, it is an aspect of one or more embodiments to provide an improved vaginal dilator which is capable of controlling the operation of a light source to overcome at least one defect in the prior art as described above.

The foregoing and/or other aspects may be achieved by providing a vaginal dilator comprising an upper dilating member and a lower dilating member that are hinged to each other, the upper dilating member comprising an upper dilating leaf and an upper press rod arranged at a tail portion of the upper dilating leaf, and the lower dilating member comprising a lower dilating leaf and a lower press rod arranged at a tail portion of the lower dilating leaf The upper dilating leaf and the upper press rod may be separately arranged, the upper dilating leaf being hinged to the upper press rod. The upper press rod may be hinged to the lower dilating member. The upper press rod may be provided with a light emitting element, a switch, and a power source, the switch being connected with the light emitting element such that when the upper dilating leaf is pressed down to contact and mate with the upper press rod or when the upper dilating leaf is disengaged from the upper press rod, may be connected to or disconnected from the power source.

The foregoing and/or other aspects may e achieved by pressing the upper dilating leaf down to contact and mate with the upper press rod, and meanwhile the upper dilating leaf contacts with the upper press rod to coordinately control the switch to be connected to the power source, thereby operating the light source. When the vaginal dilator is not in use, the upper dilating leaf is disengaged from the upper press rod to coordinately control the switch to be disconnected from the power source, thereby turning off the light source when the vaginal dilator is not in use. According to the present invention, operation of the light source may be implemented by opening or closing the upper dilating leaf, which is favorable to control of the light source and operation of the vaginal dilator by a medical staff. In addition, the The light source may be arranged on the upper press rod and the position of the light source is close to the front of the upper press rod, such that an irradiation range of the light source extends to the entire vagina.

The lower dilating leaf may be integrally formed with the lower press rod, which is favorable to achieving a compact structure The switch may be an extended elastic conductive wire connected to one terminal of the light emitting element, and may be arranged above a pole of the power source. The upper dilating leaf may be pressed down to contact and mate with the upper press rod or the upper dilating leaf may be disengaged from the upper press rod to coordinately control connection or disconnection between the extended elastic conductive wire and the power source. The other terminal of the light emitting element is connected to the other pole of the power source. The extended elastic conductive wire connected to one terminal of the light emitting element is used as the switch, and may coordinately mate with the upper dilating leaf, which is simple in fabrication and convenient in operation.

The foregoing and/or other aspects may be achieved by providing the upper dilating leaf with a light source trigger configured to abut against the extended elastic conductive wire. When the upper dilating leaf contacts and mates with the upper press rod, a light source is triggered, and when the upper dilating leaf is disengaged from the upper press rod, the light source resumes to an off state.

The light source trigger may be a protrusion member arranged on a bottom surface of the upper dilating leaf and may correspond to the position of the switch when contacting with the upper press rod. When the upper dilating leaf is pressed down, the protrusion member contacts with the extended elastic conductive wire, that is, the switch, such that the light emitting element may be connected to the power source, thereby triggering the switch.

The foregoing and/or other aspects may be achieved by providing the upper dilating leaf with a light source trigger comprising a metal sheet which is configured to provide electrical contact between one pole of the power source and a terminal of the light emitting element when the upper press rod is operated to mate the upper press rod with the upper leaf.

A locating and limiting bar may be arranged between the upper press rod and the lower press rod. During gynecologic examination, when the vaginal dilator opens to a suitable extent, the locating and limiting bar defines and fixes opening of the vaginal dilator, favorable for examination by a doctor.

The light emitting element may be an LED lamp, which is compact and does not occupy a main portion of the upper press rod, thereby preventing the view passage from blockage during examination.

The power source may be a button cell, which is compact and may mate with the LED lamp for use.

The button cell may be detachably arranged on a top portion of the upper press rod, wherein the cell may be replaced or removed for reuse.

The upper dilating leaf and the upper press rod may be separately arranged and are hinged to each other, and the upper dilating leaf may be detachable from the upper press rod so that the light source and other elements may be checked for inspection and repair.

BRIEF DESCRIPTION OF THE DRAWINGS

The above and/or other aspects will be more apparent by describing in detail exemplary embodiments, with reference to the accompanying drawings, in which.

DETAILED DESCRIPTION OF THE PREFERRED EMBODIMENTS

Figure 1:
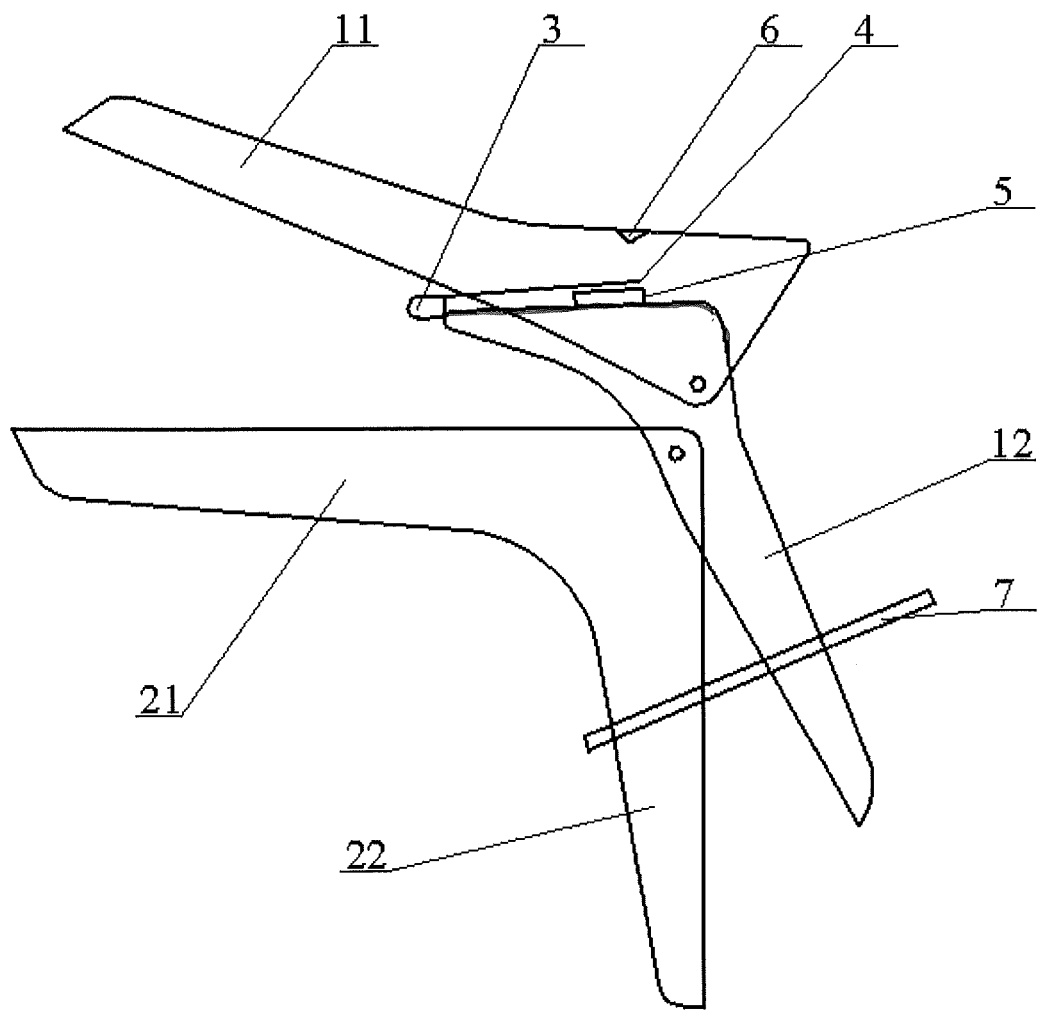
FIG. 1 is a schematic structural view of a vaginal dilator for use in gynecologic examination according to one or more embodiments.

Reference will now be made in detail to the embodiments, examples of which are illustrated in the accompanying drawings, wherein like reference numerals refer to the like elements throughout. The embodiments are described below to explain the present invention by referring to the figures. The drawings are for illustration purpose only, and shall not be construed as limitations to the present invention. For better illustration of the following embodiments, some parts or components would be omitted, scaled up or scaled down in the drawings, which are not indicative of the practical sizes. For a person skilled in the art, it shall be understandable that some commonly known structures and description thereof are omitted for brevity.

Figure 2:
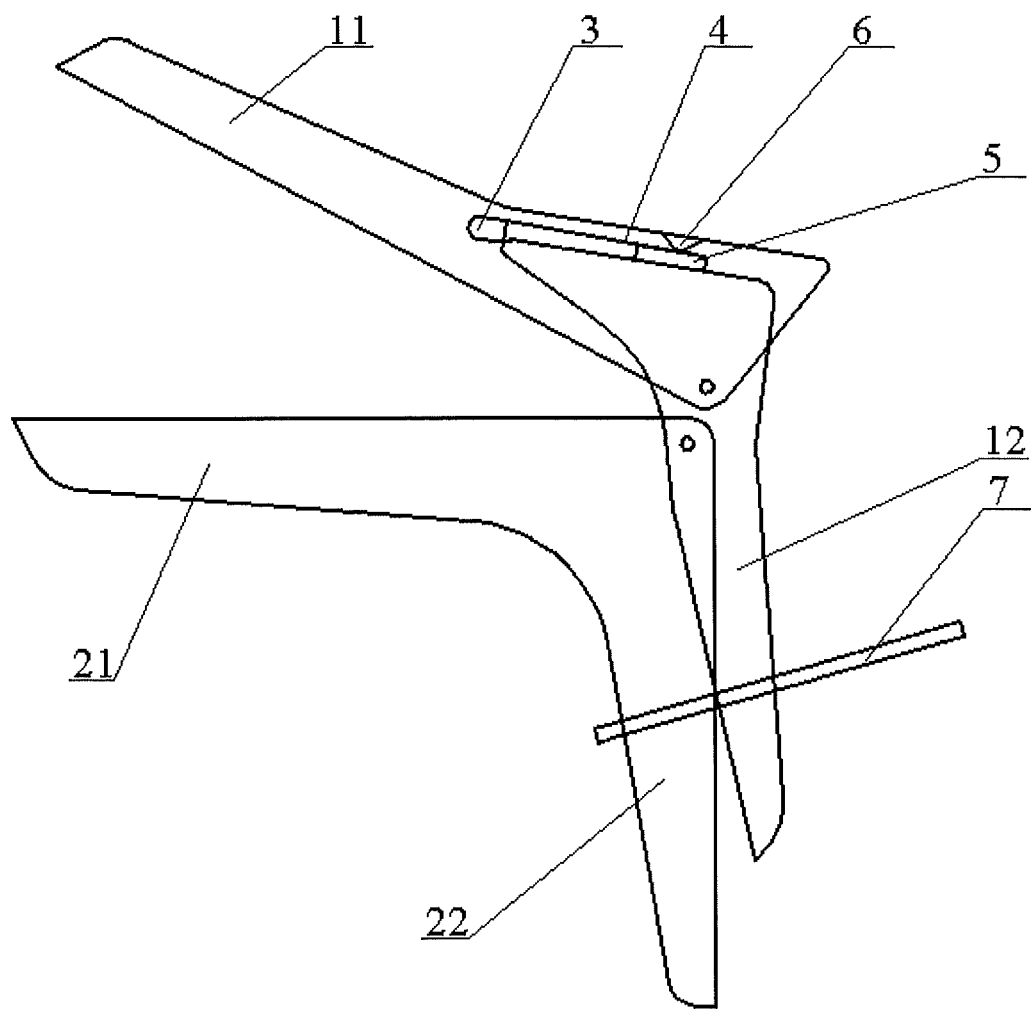
FIG. 2 is a schematic structural view of contact and mating of an upper dilating leaf with an upper press rod of the vaginal dilator according to one or more embodiments.
Figure 3:
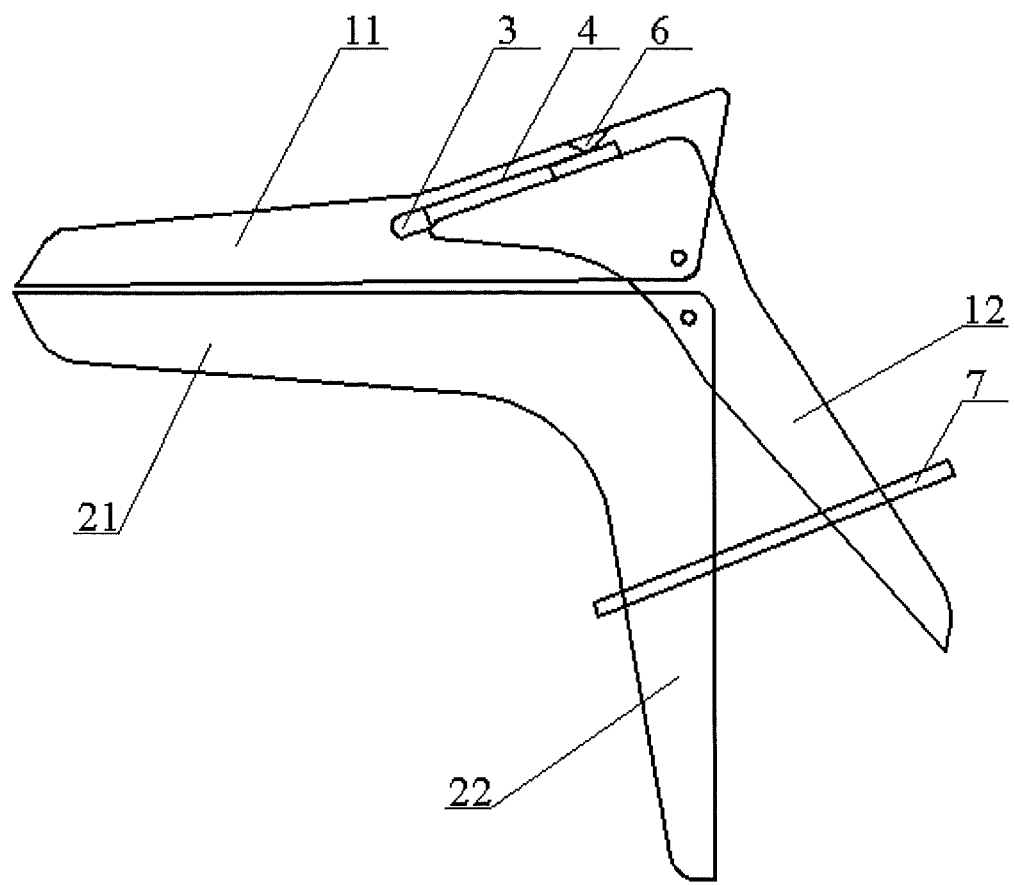
FIG. 3 is a schematic structural view when an upper dilating member and a lower dilating member of the vaginal dilator are closed according to one or more embodiments.
Figure 4:
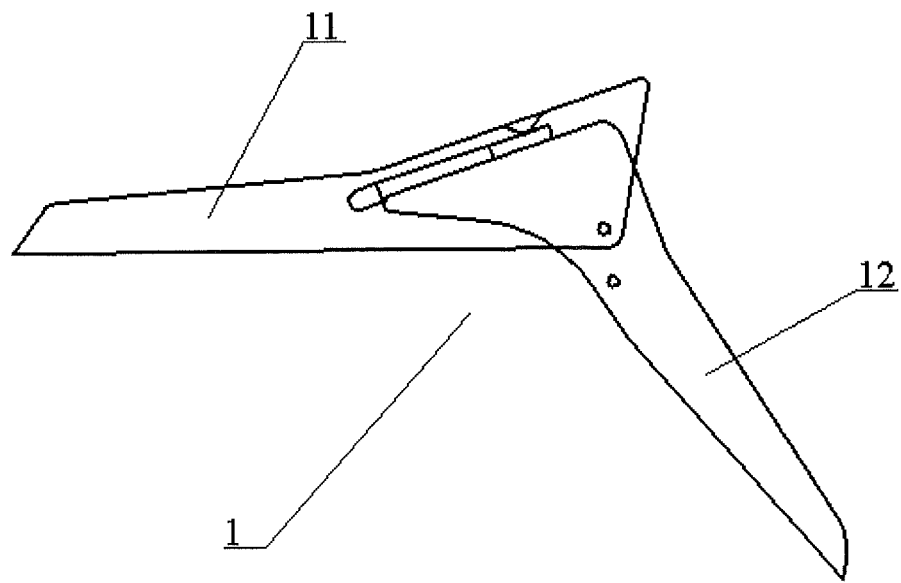
FIG. 4 is a schematic structural view of the upper dilating member of the vaginal dilator according to one or more embodiments.
Figure 5:
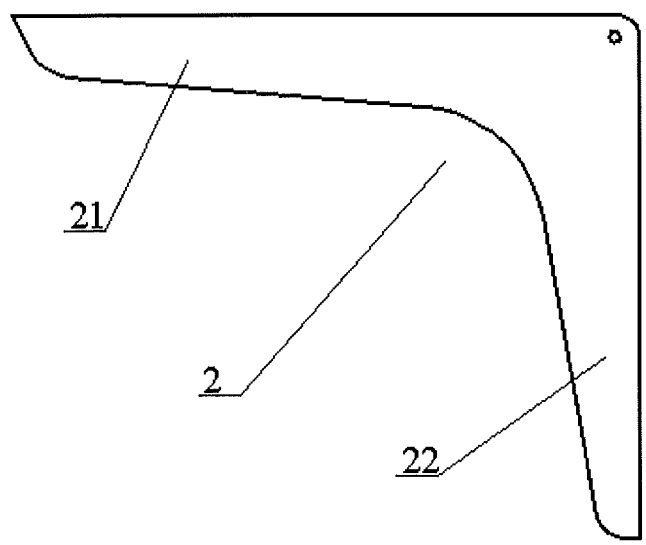
FIG. 5 is a schematic structural view of the lower dilating member of the vaginal dilator according to one or more embodiments.

Referring to FIG. 1 to FIG. 5, a vaginal dilator according to one or more embodiments comprises an upper dilating member 1 and a lower dilating member 2 that are hinged to each other, wherein the upper dilating member 1 comprises an upper dilating leaf 11 and an upper press rod 12 arranged at a tail portion of the upper dilating leaf 11, and the lower dilating member 2 comprises a lower dilating leaf 21 and a lower press rod 22 arranged at a tail portion of the lower dilating leaf 21. The upper dilating leaf 11 and the lower dilating leaf 21 may be duckbill leaves configured to dilate an examination orifice, and opening between the upper dilating leaf 11 and the lower dilating leaf 21 may be adjusted by handheld-controlling the upper press rod 12 and the lower press rod 22.

The upper dilating leaf 11 may be hinged to the upper press rod 12, and the upper press rod 12 may be hinged to the lower dilating member. The upper press rod 12 may further be provided with a light emitting element 3, a switch 4 and a power source 5, wherein the switch 4 may be connected to the light emitting element 3. The lower dilating leaf 21 may be integrally formed with the lower press rod 22, and the upper dilating leaf 11 may be pressed down to contact and mate with the upper press rod 12 at a portion corresponding to the location of the switch or the upper dilating leaf 11 may be disengaged from the upper press rod 12 to coordinately control the switch 4 to be connected to or disconnected from the power source 5.

According to one or more embodiments, the switch 4 may be an extended elastic conductive wire connected to one terminal of the light emitting element 3, and is arranged above a pole of the power source 5. The upper dilating leaf 11 may be pressed down to contact and mate with the upper press rod 12 or the upper dilating leaf 11 may be disengaged from the upper press rod 12 to coordinately control connection or disconnection between the extended elastic conductive wire and the power source 5. The other terminal of the light emitting element 3 may be directly connected to the other pole of the power source 5. This arrangement is advantageous because it is simple in both manufacture and operation.

Further, the upper dilating leaf 11 may be provided with a light source trigger 6 configured to abut against the extended elastic conductive wire. When the upper dilating leaf 11 contacts and mates with the upper press rod 12, the light source is triggered, and when the upper dilating leaf 11 is disengaged from the upper press rod 12, the light source resumes to an off state. The light source trigger 6 may be a protrusion member arranged on a bottom surface of the upper dilating leaf 11, and the light source trigger 6 corresponds to the position of the switch 4 when contacting with the upper press rod 12. When the upper dilating leaf 11 is pressed down, the protrusion member contacts with the extended elastic conductive wire or the switch 4, such that the light emitting element 3 is connected to the power source, thereby triggering the switch 4.

Further, the light emitting element 3 may be an LED lamp, which is compact, does not occupy a main portion of the upper press rod 12, and abuts against the upper dilating leaf 11 during work, thereby preventing the view passage from blockage during examination. In addition, the power source 5 may be a button cell detachably arranged on a top portion of the upper press rod 12, which may be replaced or removed for reuse.

Further, a locating and limiting bar 7 may be arranged between the upper press rod 12 and the lower press rod 22. During gynecologic examination, when the vaginal dilator opens to a suitable extent, the locating and limiting bar 7 defines and fixes opening of the vaginal dilator, favorable for examination by a doctor.

The vaginal dilator works under the following principles: During gynecologic examination, a doctor places the vaginal dilator into the vagina of a patient, and adjusts opening between the upper dilating leaf 11 and the lower dilating leaf 21 by handheld-controlling the upper press rod 12 and the lower press rod 22, thereby dilating the examination orifice. The doctor may enable the upper dilating leaf 11 to contact and mate with the upper press rod 12, such that the light source trigger triggers the switch 4 of the light source to turn on the light source, and then the doctor performs the examination operations. Alternatively, the doctor directly performs the examination operations, and during dilating the examination orifice, due to pressure, the upper dilating leaf 11 automatically contacts and mates with the upper press rod 12 to trigger the switch 4 of the light source, such that the light source is turned on. Upon completion of the examination, the light source trigger 6 may be separated from the switch 4 after the upper dilating leaf 11 is disengaged from the upper press rod 12, such that the switch 4 is disconnected and thus the light source is closed.

During the operation, the upper dilating leaf 11 and the upper press rod 12 may be separately arranged and hinged to each other. The upper dilating leaf 11 may be detached from the upper press rod 12, and light source-specific elements may be checked for inspection and repair. Since the light emitting device 3, the switch 4 and the power source 5 are consumables, during manufacture, transportation and placement, these components or elements may be prone to failure. Therefore, in this way, the problem that a vaginal dilator is discarded only due to failure of some replaceable elements or components may be avoided.

According to one or more embodiments, the light source trigger 6 may be a metal sheet arranged on a bottom surface of the upper dilating leaf 11. When the upper dilating leaf 11 contacts with the upper press rod 12, the two ends of the metal sheet respectively correspond to a connector at one end of the light emitting element 3 and the position of one pole of the power source 5. When the upper dilating leaf 11 is pressed down, the two ends of the metal sheet may be respectively connected to the connector at one end of the light emitting element 3 and one pole of the power source 5, such that a conductive loop is formed between the power source 5 and the light emitting element 3, thereby achieving conduction of the circuit of the LED lamp. The other structures according to this embodiment and working principles thereof are similar to those described in Embodiment 1, which are thus not described herein any further.

According to one or more embodiments, the upper dilating leaf 11 is provided with a light emitting element 3, a switch 4, and a power source 5. The upper dilating leaf 11 may be pressed down to contact and mate with the upper press rod or the upper dilating leaf is disengaged from the upper press rod to coordinately control the switch to be connected to or disconnected from the power source. The upper press rod 12 may be provided with a light source trigger 6 configured to abut against the switch.

While aspects of the present invention have been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. A vaginal dilator for use in gynecologic examination, comprising: an upper dilating member; and
a lower dilating member which is hinged using a first hinge to the upper dilating member;
wherein the upper dilating member comprises:
an upper dilating leaf; and
an upper press rod arranged at a tail portion of the upper dilating leaf,
wherein the lower dilating member comprises:
a lower dilating leaf and
a lower press rod arranged at a tail portion of the lower dilating leaf;
wherein the upper dilating leaf and the upper press rod are separately arranged;
wherein the upper dilating leaf is hinged to the upper press rod using a second hinge which is non-coaxial to the first hinge, and the upper press rod is hinged using the first hinge to the lower dilating member;
wherein the upper press rod is provided with a light emitting element, a switch, and a power source, the switch being connected to the light emitting element;
wherein the upper dilating leaf is pivotally operated about the second hinge to contact and mate with the upper press rod to control the switch to be connected to the power source, and
wherein the upper dilating leaf is pivotally operated about the second hinge to disengage from the upper press rod to control the switch to be disconnected from the power source.

2. The vaginal dilator according to claim 1, wherein the lower dilating leaf is integrally formed with the lower press rod.

3. The vaginal dilator according to claim 1, wherein the switch is an extended elastic conductive wire connected to a first terminal of the light emitting element, and is arranged above a first pole of the power source;
wherein when the upper dilating leaf is pressed down to contact and mate with the upper press rod, the extended elastic conductive wire is connect to the power source, and when the upper dilating leaf is disengaged from the upper press rod the extended elastic conductive wire is disconnected from the power source; and
wherein a second terminal of the light emitting element is connected to a second pole of the power source.

4. The vaginal dilator according to claim 3, wherein the upper dilating leaf is provided with a light source trigger configured to abut against the extended elastic conductive wire.

5. The vaginal dilator according to claim 4, wherein the light source trigger is a protrusion member arranged on a bottom surface of the upper dilating leaf, and the upper dilating leaf corresponds to the position of the switch when contacting with the upper press rod.

6. The vaginal dilator according to claim 1, wherein a locating and limiting bar is arranged between the upper press rod and the lower press rod.

7. The vaginal dilator according to claim 1, wherein the light emitting element is an LED lamp.

8. The vaginal dilator according to claim 1, wherein the power source is a button cell.

9. The vaginal dilator according to claim 8, wherein the button cell is detachably arranged on a top portion of the upper press rod.

10. The vaginal dilator according to claim 1, wherein the light emitting element is arranged near a front end of the upper press rod.

11. The vaginal dilator according to claim 1, wherein the upper dilating leaf is pivotally operated to contact and mate with the upper press rod by pressing down on the upper dilating leaf.

12. The vaginal dilator according to claim 1, wherein the upper dilating leaf is configured to be pivotally operated to contact and mate with the upper press rod by operating the upper press rod and lower press rod to open an examination orifice, the examination orifice providing pressure on the upper dilating leaf.

13. The vaginal dilator according to claim 1, wherein the contacting and mating of the upper press rod with the upper dilating leaf and also the disengaging of the upper press rod from the upper dilating leaf operates with a resistive click.

14. A vaginal dilator for use in gynecologic examination, comprising:
- an upper dilating member; and
- a lower dilating member which is hinged using a first hinge to the upper dilating member;
- wherein the upper dilating member comprises:
  - an upper dilating leaf; and
  - an upper press rod arranged at a tail portion of the upper dilating leaf,
- wherein the lower dilating member comprises:
  - a lower dilating leaf and
  - a lower press rod arranged at a tail portion of the lower dilating leaf;
- wherein the upper dilating leaf and the upper press rod are separately arranged;
- wherein the upper dilating leaf is hinged to the upper press rod using a second hinge which is non-coaxial to the first hinge, and the upper press rod is hinged using the first hinge to the lower dilating member;
- wherein the upper press rod is provided with a light emitting element, a switch, and a power source, the switch being connected to the light emitting element, and the light emitting element being connected to a pole of the power source;
- wherein the upper dilating leaf is pivotally operated about the second hinge to contact and mate with the upper press rod to control the switch to be connected to the power source,
- wherein the upper dilating leaf is pivotally operated about the second hinge to disengage from the upper press rod to control the switch to be disconnected from the power source, and
- wherein the upper press rod is provided with a light source trigger configured to abut against the switch.

* * * * *